US012589082B2

(12) United States Patent
Zeilkha et al.

(10) Patent No.: US 12,589,082 B2
(45) Date of Patent: Mar. 31, 2026

(54) COMPOSITIONS COMPRISING THYMOQUINONE AND ADDITIONAL BIOLOGICALLY ACTIVE COMPOUNDS

(71) Applicant: N.S. OILS LTD., Kibbutz Sa'ad (IL)

(72) Inventors: Mor Zeilkha, Ramat Gan (IL); Dan Rapaport, Kfar Haroe'e (IL)

(73) Assignee: N.S. OILS LTD., Kibbutz Sa'ad (IL)

( * ) Notice: Subject to any disclaimer, the term of this patent is extended or adjusted under 35 U.S.C. 154(b) by 1002 days.

(21) Appl. No.: 17/425,483

(22) PCT Filed: Jan. 27, 2020

(86) PCT No.: PCT/IL2020/050102
§ 371 (c)(1),
(2) Date: Jul. 23, 2021

(87) PCT Pub. No.: WO2020/157748
PCT Pub. Date: Aug. 6, 2020

(65) Prior Publication Data
US 2022/0087953 A1 Mar. 24, 2022

Related U.S. Application Data

(60) Provisional application No. 62/797,394, filed on Jan. 28, 2019.

(51) Int. Cl.
| | |
|---|---|
| *A61K 31/122* | (2006.01) |
| *A61K 31/00* | (2006.01) |
| *A61K 31/015* | (2006.01) |
| *A61K 31/353* | (2006.01) |
| *A61K 36/185* | (2006.01) |

(52) U.S. Cl.
CPC .......... *A61K 31/122* (2013.01); *A61K 31/015* (2013.01); *A61K 31/353* (2013.01); *A61K 31/658* (2023.05); *A61K 36/3482* (2024.05)

(58) Field of Classification Search
CPC .. A61K 31/122; A61K 31/015; A61K 31/353; A61K 36/185
See application file for complete search history.

(56) References Cited

U.S. PATENT DOCUMENTS

| | | | | |
|---|---|---|---|---|
| 11,426,365 | B2 * | 8/2022 | Sela | A61K 36/71 |
| 11,883,455 | B2 * | 1/2024 | Albert | A61K 9/0053 |
| 2018/0125914 | A1 * | 5/2018 | Madhavamenon | A61K 36/71 |

FOREIGN PATENT DOCUMENTS

| | | | | |
|---|---|---|---|---|
| DE | 202005007603 U1 * | 9/2005 | | A61K 8/922 |
| WO | WO-2019016794 A1 * | 1/2019 | | A61K 31/122 |
| WO | WO-2019180719 A1 * | 9/2019 | | A61K 36/71 |

OTHER PUBLICATIONS

George, B. and Kumaran, B. "Protective effect of Nigella sativa oil and Astaxanthin on Monosodium glutamate Induced dyslipidemia in Rats", Int. Arch. App. Sci. Technol., vol. 6, Dec. 2015, p. 1-7. (Year: 2015).*
Machine translation for DE202005007603U1. Espacenet, Accessed Sep. 2024, p. 1-15. (Year: 2005).*
Amin, Bahareh, and Hossein Hosseinzadeh. "Black Cumin (*Nigella sativa*) and its Active Constituent, Thymoquinone: An Overview on the Analgesic and Anti-Inflammatory Effects." Planta Medica, vol. 82, No. 01/02, Jan. 2016, pp. 8-16. (Year: 2016).*
Mohammed, Nameer Khairullah, et al. "The Effects of Different Extraction Methods on Antioxidant Properties, Chemical Composition, and Thermal Behavior of Black Seed (*Nigella sativa* L.) Oil." Evidence-Based Complementary and Alternative Medicine: eCAM, vol. 2016, 2016, p. 6273817. (Year: 2016).*
Semiha Dede et al: "In vitro Evaluation of Thymoquinone and Lycopene Supplementation on Oxidative DNA Damage and Oxidant Status in High Glucose Conditions", Latin American Journal of Pharmacy, Jan. 1, 2019, pp. 2383-2362, XP055686173.
Binu George et al: "Protective effect of Nigella sativa oil and Astaxanthin on Monosodium glutamate Induced dyslipidemia in Rats", International Archive of Applied Sicences and Technology, Dec. 1, 2015, pp. 1-7. DOI: 10.15515/iaast.0976.
Said Gharby et al: "Chemical investigation of *Nigella sativa* L. seed oil produced in Morocco", Journal of The Saudi Society of Agricultural Sciences, vol. 14, No. 2, Dec. 11, 2013, pp. 172-177. DOI: 10.1016/j.jssas.2013.12.001.
Khan Ma: "Chemical composition and medicinal properties of Nigella sativa Linn.", Inflammopharmacology, vol. 7, Mar. 1999, pp. 15-35. DO: 10.1007/s10787-999-0023-y.
Feakes J.: "Health Benefits of Cannabis and Black Seed Oil", retrieved from the internet at URL <https://greendorphin.com/benefits-of-cannabis-and-black-seed-oil/>, (retrieved on Dec. 31, 2024), Dec. 10, 2018.
Gonzalez M. et al.: "Barrington and TriNutra help launch blend of ThymoQuin and Pycnogenol", retrieved from the internet at URL:<https://nutraceuticalbusinessreview.com/barrington-and-trinutra-help-launch-blend-ofthymoquin-and-pycnogenol-161227>, (retrieved on Jan. 15, 2025),Sep. 1, 2020.
Burstein S.: "Cannabidiol (CBD) and its analogs: a review of their effects on inflammation", Bioorg. Med. Chem. 23(7):pp. 1377-1385 (2015).

(Continued)

*Primary Examiner* — Clinton A Brooks
*Assistant Examiner* — Kyle Nottingham
(74) *Attorney, Agent, or Firm* — FISHERBROYLES, LLP; Roger L. Browdy

(57) ABSTRACT

The present invention is directed to a composition comprising a combination of thymoquinone (TQ) and one or more additional biologically active agents, wherein said biologically active agents are selected from the group consisting of carotenoids, *Cannabis*-related compounds and pycnogenol. In one preferred embodiment, the TQ is contained in cold-pressed *Nigella sativa* oil, wherein said oil is characterized by a TQ concentration of at least 1.5% (w/w) and a free fatty acid (FFA) content of 3.5% (w/w) or less. The present invention is also directed to methods for treating or preventing inflammatory conditions by means of administering these compositions.

13 Claims, 10 Drawing Sheets

(56)                References Cited

OTHER PUBLICATIONS

Peng Y-J: "Pycnogenol attenuates the inflammatory and nitrosative stress on joint inflammation induced by urate crystals", Free Radic. Biol. Med. 52(4) :pp. 765-774 (2011).

* cited by examiner

COMPOSITIONS COMPRISING THYMOQUINONE AND ADDITIONAL BIOLOGICALLY ACTIVE COMPOUNDS

FIELD OF THE INVENTION

The present invention is related to compositions comprising combinations of thymoquinone and other biologically active agents. More specifically, the invention discloses compositions comprising combinations of *Nigella sativa* oil containing thymoquinone, with cannabinoids, carotenoids or the maritime pine bark extract Pycnogenol.

BACKGROUND OF THE INVENTION

*Nigella sativa* (NS), also known by a variety of other names, including black cumin, black seed and black caraway is an annual flowering plant indigenous to the Middle East and other regions of southwest Asia. Since antiquity, the seeds and other parts of the plant have been used as a remedy for many different ailments. More recently, there has been a revival of interest in the use of NS seeds and of various oils and other preparations derived therefrom, for the treatment of a large number of conditions and as a supplement for use in the maintenance of good health.

Among the therapeutic properties associated with, or attributed to, NS, the most widely known are its anti-inflammatory, anti-cancer, anti-bacterial, anti-fungal, blood pressure reducing and blood sugar lowering activities.

Many, but not all, of the pharmacologically active agents are present in the oil contained within the NS seed. In fact, the seeds of this plant contain two distinguishable oil fractions: fixed oil and essential oil, the latter containing a mixture of highly active volatile agents. Among these volatiles, one of the most highly active components is thymoquinone (TQ), and many of the pharmacological activities of NS oil-derived compositions are attributable to this agent.

Despite the fact that NS oil contains many biologically active substances, the present inventors have unexpectedly found that some of the pharmacological effects associated with NS oil may be synergistically enhanced when said oil is combined with certain other substances and agents of natural origin.

SUMMARY OF THE PRESENT INVENTION

The present inventors have unexpectedly found that compositions comprising combinations of NS oil and certain additional biologically active substances possess synergistic anti-inflammatory properties. Furthermore, the inventors have found that this synergistic interaction is observed only when the thymoquinone (TQ) concentration of the composition is above a certain level, as will be described hereinbelow. In addition, said synergistic interaction is also observed when the composition comprises a combination of the additional biologically substance(s) and TQ, even when said TQ is not present in the form of one of the components of NS oil, but rather when in a different form, such as synthetic TQ, or TQ present in oils and extracts of other non-NS species.

Thus, in its most general form, the present invention is directed to a composition comprising a combination of thymoquinone (TQ) and one or more additional biologically active agents. Preferably, said biologically active agents are selected from the group consisting of carotenoids, *Cannabis*-related compounds and pycnogenol.

In one aspect, the present invention is directed to compositions comprising a combination of TQ and one or more carotenoids. Preferably, the combination is selected such that there is a synergistic enhancement of the biological effects caused by either the TQ or carotenoids alone. In particular, the synergistic enhancement is a synergistic enhancement of anti-inflammatory activity. In one embodiment, said synergistic enhancement is due to a synergistic interaction between TQ (either contained within NS oil or when provided as synthetic TQ) and one or more carotenoids with respect to the ability of those agents to inhibit the production of the inflammatory mediator nitric oxide (NO).

The present invention is thus, in one aspect, directed to compositions comprising a combination of thymoquinone (TQ) and one more carotenoids. TQ is one of the major bioactive compounds present in NS oil. However, for the purpose of the present invention, the TQ used in the compositions disclosed herein may be either synthetic TQ or natural TQ obtained from a plant source, particularly *Nigella sativa*. Other suitable plant species which may also be used to provide the TQ for this aspect of the invention include (but are not limited to) *Origanum vulgare* (oregano) and *Thymus vulgaris* (thyme).

While any of the naturally occurring or synthetic carotenoids may be used in this aspect of the invention, in one preferred embodiment, the one or more carotenoids are selected from the group consisting of lutein, beta-carotene, astaxanthin, lycopene, phytoene, phytofluene, fucoxanthin and zeta-carotene. In one embodiment, the one or more carotenoids comprise lutein. In another embodiment, the carotenoid components comprises beta-carotene. In yet another embodiment, the carotenoid component comprises astaxanthin.

The carotenoids used to prepare the composition of the present invention may be either synthetic carotenoids, or carotenoids obtained from natural sources, such as various fruit and vegetables (e.g. tomatoes in the case of lycopene, phytoene, phytofluene and beta-carotene) and other plants (e.g. the African marigold plant in the case of lutein). Astaxanthin may be used either in its synthetic form, or isolated and purified from various natural sources, notably from certain species of microalgae (e.g. *Haematococcus pluvialis*) and yeast (e.g. *Xanthophyllomyces dendrorhous*). Fucoxanthin may be obtained from natural sources such as various brown seaweeds, including those of the genii *Fucus, Dictyota*, and *Laminaria*. In embodiments in which the composition comprises more than one carotenoid, combinations of synthetic versions of some carotenoids with other carotenoids derived from plant or microbial species may be used.

In another aspect, the present invention is directed to compositions comprising a combination of NS oil and one or more biologically active compounds present in, or associated with, the *Cannabis* plant.

Preferably, the combination is selected such that there is a synergistic enhancement of the biological effects caused by either the NS oil or *Cannabis*-derived compounds alone. In particular, the synergistic enhancement is a synergistic enhancement of anti-inflammatory activity. In one embodiment, said synergistic enhancement is due to a synergistic interaction between NS oil and one or more biologically active compounds present in the *Cannabis* plant with respect to the ability of those agents to inhibit the production of the inflammatory mediator nitric oxide (NO).

The present invention is also directed to compositions comprising a combination of thymoquinone (TQ) and one more *Cannabis*-associated biologically active compounds.

TQ is one of the major bioactive compounds present in NS oil. However, for the purpose of the present invention, the TQ used in the compositions disclosed herein may be either synthetic TQ or natural TQ obtained from a plant source, particularly *Nigella sativa*. Other suitable plant species which may also be used to provide the TQ for this aspect of the invention include (but are not limited to) *Origanum vulgare* (oregano) and *Thymus vulgaris* (thyme).

In one preferred embodiment, the concentration of TQ in the composition is 1.5% (w/w) or more.

In one preferred embodiment of this aspect of the invention, the one or more *Cannabis*-derived biologically active compounds are cannabinoids.

In one particularly preferred embodiment the cannabinoid is cannabidiol (CBD). CBD is conveniently incorporated into the composition of the present invention in the form of CBD oil. However, other physical forms of CBD may also be used to prepare the present composition, including, for example, hemp extract, which is form of CBD used in one preferred embodiment of this aspect of the present invention.

It is to be noted that although for the purpose of brevity CBD, other cannabinoids and other *Cannabis*-associated compounds are referred to herein as 'biologically active compounds present in the *Cannabis* plant', '*Cannabis*-related compounds', '*Cannabis*-derived biologically active compounds', or the like, said compounds used to prepare the composition of the present invention are not necessarily derived from the *Cannabis* plant, or from any other plant species. Thus, while in one preferred embodiment, the cannabinoids and/or other *Cannabis*-related compounds are extracted or isolated from a species of the *Cannabis* genus (e.g. *Cannabis sativa* or *Cannabis* indica). However, in other preferred embodiments the cannabinoids and other *Cannabis*-associated active compounds may be synthetic in origin.

In another aspect, the present invention is directed to compositions comprising a combination of NS oil and the biologically active agent known as 'pycnogenol'. Pycnogenol is a food supplement derived from extracts of the bark of the maritime pine tree (*Pinus pinaster*) and is standardized to contain 70% procyanidin. TQ is one of the major bioactive compounds present in NS oil. However, for the purpose of the present invention, the TQ used in the compositions disclosed herein may be either synthetic TQ or natural TQ obtained from a plant source, particularly *Nigella sativa*. Other suitable plant species which may also be used to provide the TQ for this aspect of the invention include (but are not limited to) *Origanum vulgare* (oregano) and *Thymus vulgaris* (thyme).

In one preferred embodiment, the concentration of TQ in the composition is 1.5% (w/w) or more.

In one preferred embodiment of any of the compositions comprising TQ and an additional biologically active agent disclosed hereinabove, the concentration of TQ in the composition is 1.5% (w/w) or more. In another preferred embodiment, the concentration of TQ in the composition is 2% (w/w) or more. In another preferred embodiment, the concentration of TQ in the composition is 3% (w/w) or more. In a further preferred embodiment, the concentration of TQ in the composition is 3% (w/w). In still other preferred embodiments, the TQ concentration may be greater than 3% (w/w).

In one preferred embodiment of any of the compositions comprising TQ and an additional biologically active agent disclosed hereinabove, the TQ is synthetic TQ. In another preferred embodiment, the TQ is present in, or obtained from, a plant source selected from the group consisting of

*Nigella sativa, Origanum vulgare* and *Thymus vulgaris* or fermented TQ. In one particularly preferred embodiment, the TQ is present in *Nigella sativa* (NS) oil, most preferably, cold-pressed NS oil. For the purpose of the present invention, the NS oil has a TQ concentration of at least 1.5% (w/w) and a free fatty acid (FFA) content of 3.5% (w/w) or less. A description of a suitable cold-pressed NS oil, a method for its production, may be found in the co-owned international patent application which published as WO2019180719, the contents of which are incorporated herein in their entirety.

In some embodiments, the TQ concentration of the NS oil is, as disclosed above, at least 1.5% (w/w). In other embodiments, the TQ concentration is at least 2% (w/w). Also, as disclosed hereinabove, the FFA concentration of the NS oils which may be used to work the present invention may be 3.5% (w/w) or less. However, in some preferred embodiments, the FFA concentration may be 2% or less. In one particularly preferred embodiment, the FFA concentration is 1.7% (w/w). Without wishing to bound by theory, the present inventors believe that the synergistic interaction observed between NS oil and the additional biologically active agents disclosed hereinabove is obtained only when the NS oil used is characterized by aforesaid high TQ and low FFA concentrations. Thus, in one preferred embodiment, weight ratio of FFA to TQ is equal to or less than 2.33:1. In another preferred embodiment, the weight ratio of FFA to TQ is equal to or less than 1:1. In a still further preferred embodiment, the weight ratio of FFA to TQ is about 0.57:1.

Preferably, the above-disclosed compositions of the present invention are characterized by synergism between said TQ and said agents, with respect to their anti-inflammatory activities. The term 'synergistic interaction' is used herein to refer to the type of interaction that leads to biological effects (in this case, anti-inflammatory activity) of a combination of TQ and the other agents which are numerically greater than the sum of the effects caused by each component (i.e. TQ and additional agent) when tested alone. In a preferred embodiment, the anti-inflammatory activity for which a synergistic interaction is seen in the present invention is the inhibition of nitric oxide (NO) production.

In another aspect, the present invention provides a method for treating, inhibiting or preventing inflammatory diseases or disorders comprising administering to a mammalian subject in need of such treatment any of the compositions disclosed herein. It is to be noted that this method also includes within its scope the treatment, prevention and/or inhibition of the inflammatory aspects of diseases and disorders which are not entirely inflammatory in nature, but which are characterized by, inter alia, inflammatory aspects.

DETAILED DESCRIPTION OF PREFERRED EMBODIMENTS

Figure 1:
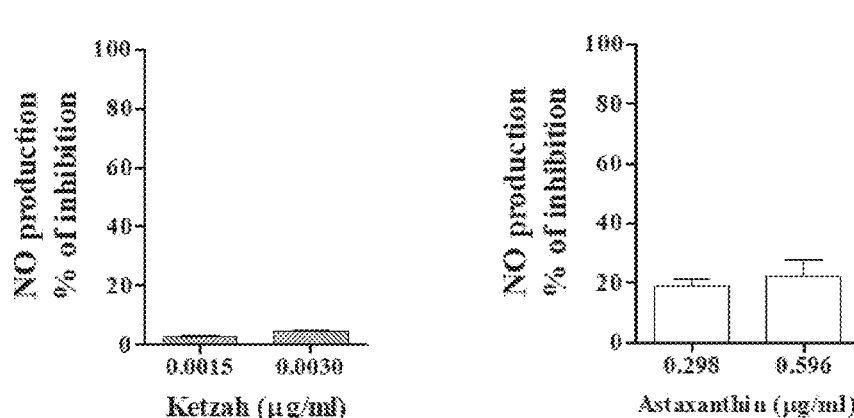
FIG. 1 graphically presents results showing the inhibitory effect of combinations of TG and astaxanthin on NO production.
Figure 1:
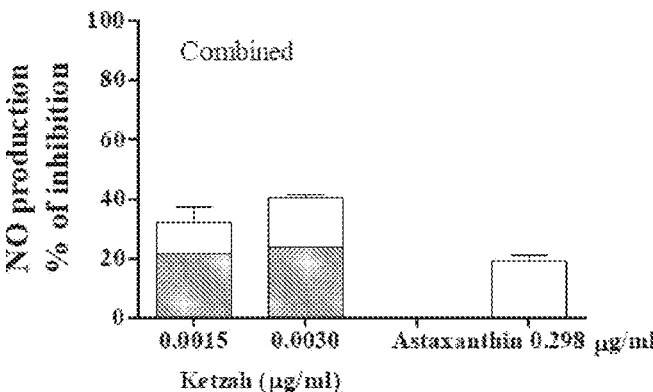
Figure 1:
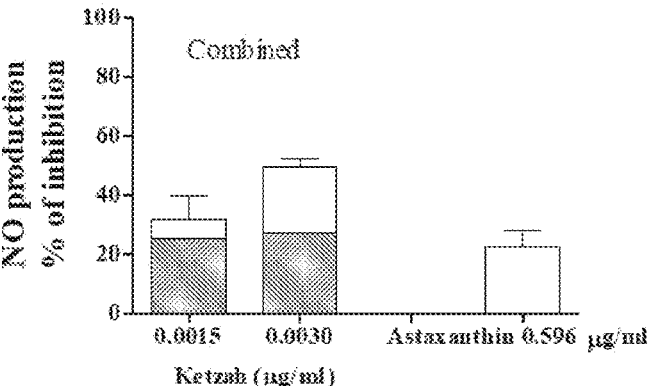

Many different anti-inflammatory compositions comprising combinations of TQ and additional biologically active agents, as disclosed hereinabove, are included within the scope of the present invention. These include (but are, of course, not limited to) the following compositions:

A composition comprising TQ and astaxanthin, wherein said TQ is present in cold-pressed NS oil, wherein the concentration of said TQ in said composition is at least 1.5% (w/w), and wherein said composition further comprises FFA at a concentration of no more than 3.5% (w/w). In one preferred embodiment of this composition, the TQ concentration is about 3% (w/w), the FFA concentration is 1.7% and the concentration of astaxanthin is about 15% (w/w).

A composition comprising TQ and lutein, wherein said TQ is present in cold-pressed NS oil, wherein the concentration of said TQ in said composition is at least 1.5% (w/w), and wherein said composition further comprises FFA at a concentration of no more than 3.5% (w/w). In one preferred embodiment of this composition, the TQ concentration is 3% (w/w) and the FFA concentration is 1.7%.

A composition comprising TQ and lycopene, wherein said TQ is present in cold-pressed NS oil, wherein the concentration of said TQ in said composition is at least 1.5% (w/w), and wherein said composition further comprises FFA at a concentration of no more than 3.5% (w/w). In one preferred embodiment of this composition, the TQ concentration is 3% (w/w) and the FFA concentration is 1.7%.

A composition comprising TQ and CBD, wherein said TQ is present in cold-pressed NS oil, wherein the concentration of said TQ in said composition is at least 1.5% (w/w), and wherein said composition further comprises FFA at a concentration of no more than 3.5% (w/w). In one preferred embodiment of this composition, the TQ concentration is 3% (w/w) and the FFA concentration is 1.7%.

A composition comprising TQ and pycnogenol, wherein said TQ is present in cold-pressed NS oil, wherein the concentration of said TQ in said composition is at least 1.5% (w/w), and wherein said composition further comprises FFA at a concentration of no more than 3.5% (w/w). In one preferred embodiment of this composition, the TQ concentration is 3% (w/w) and the FFA concentration is 1.7%.

The present inventors have found that provided the TQ and FFA concentrations are controlled such that they fall within the limits defined herein, synergistic interactions between said TQ and the additional biologically active agents (with respect to anti-inflammatory activity) are seen over a very broad range of mutual weight ratios.

Thus, in one embodiment of the present invention, the additional biologically active agent is astaxanthin and the weight ratio of TQ to said astaxanthin is in the range of 1:0.1-1:500, preferably in the range of 1:1-1:200 and more preferably in the range of 1:3-1:100. Preferred values for this ratio include 1:3, 1:5, 1:40 and 1:60.

In another embodiment of the present invention, the additional biologically active agent is lutein and the weight ratio of TQ to said lutein is in the range of 1:0.01-1:500 and preferably in the range of 1:0.05-1:200.

Similarly, with the other carotenoids (such as lycopene and beta-carotene), the weight ratio between TQ and said carotenoids is in the range of 1:0.01-1:500.

In another embodiment of the present invention, the additional biologically active agent is CBD and the weight ratio of TQ to said CBD is in the range of 1:0.01-1:100 and preferably in the range of 1:0.1-1:50.

In another embodiment of the present invention, the additional biologically active agent is pycnogenol and the weight ratio of TQ to said pycnogenol is in the range of 1:0.1-1:100,000 and preferably in the range of 1:10-1:10,000.

As disclosed hereinabove, the compositions of the present invention may be used in a method to treat, inhibit or prevent inflammatory diseases, conditions, states or disorders in a mammalian subject in need of such treatment.

In one preferred embodiment, said inflammatory diseases, conditions, states or disorders are those which are mediated, at least in part, by the inflammatory mediator, nitric oxide (NO).

Non-limiting examples of such NO-related inflammatory conditions which may be treated, inhibited or prevented with the method of the present invention include: osteoarthritis, rheumatoid arthritis, asthma, rhinitis and other upper respiratory tract inflammatory conditions, adult respiratory distress syndrome (ARDS), cardiovascular inflammation, reperfusion injury, peritonitis, cirrhosis, inflammatory bowel disease, inflammatory skin disorders including psoriasis, bullous diseases, eczema, allergic reactions in the skin, inflammatory conditions of the eyes, retinopathy, inflammatory conditions of infective origin, such as sepsis, trauma and other acute inflammatory conditions, chronic inflammatory conditions, allergies and hypersensitivity reactions of all of the various tissues, organs and organ systems. Many other such inflammatory conditions may also be treated or prevented using the method of the present invention, and therefore within the scope of the present invention as claimed.

Examples of conditions and disorders which are not wholly inflammatory in nature which may be treated, inhibited or prevented by the method of the present invention include (but are not limited to): benign neoplastic conditions, malignant neoplastic conditions, cardiovascular diseases including atherosclerosis, renal disorders, metabolic disorders (e.g. diabetes mellitus) and so on.

A typical daily dose for the method of treatment disclosed above would be a single capsule containing 500 mg of the composition, of which 15 mg would be TQ. In the case of combinations of TQ with carotenoids, the daily dose of the carotenoid would typically be in the range of 1-100 mg.

In another aspect, the present invention is directed to any of the compositions disclosed hereinabove and claimed hereinbelow, for use in the treatment, inhibition or prevent of inflammatory diseases, preferably inflammatory diseases that are mediated, at least in part, by the inflammatory mediator, nitric oxide (NO), and including (but not limited to) the diseases and conditions listed above.

In a further aspect, the present invention is also directed to the use of any of the compositions disclosed hereinabove for the manufacture of a medicament for the treatment, inhibition or prevent of inflammatory diseases, preferably inflammatory diseases that are mediated, at least in part, by the inflammatory mediator, nitric oxide (NO), and including (but not limited to) the diseases and conditions listed above.

The various combinations of NS oil and additional biologically active agents of the present invention may be administered as a single composition. In other embodiments, the NS oil and the additional agents (i.e. the carotenoids or the *Cannabis*-associated compounds) may be administered separately, in different formulations. Such separate administration of the two components may be either simultaneous or sequential (in either order).

The compositions of the present invention (whether they contain the combination of the two different components, or whether said components are administered separately) may be administered systemically or topically. In one preferred embodiment, said compositions are administered orally, and for this purpose may be formulated as capsules, caplets, tablets, hard candies, gummies, liquids, taste-masked liquids, syrups and the like.

In another embodiment the compositions may be formulated for topical administration, for example as creams, ointments or lotions for application to the skin or external mucous membranes, or as pessaries for rectal or vaginal administration.

Further details of suitable formulations for use in the present invention are well known to the skilled artisan in this technical field and may be obtained from standard reference works such Remington's Pharmaceutical Sciences, Mack Publishing Co, Easton, Pa., USA (1980).

The following non-limiting working examples illustrate the anti-inflammatory effects of some of the compositions of the present invention. These examples also demonstrate the synergistic interaction between the NS oil and the other biologically active components of said compositions.

Example 1

Inhibition of the Production of Nitric Oxide (NO) by Various Combinations of NS Oil and the Carotenoids Lutein, Beta-Carotene, Lycopene and Astaxanthin The aim of this study was to investigate the effect of different combinations of NS oil and carotenoids on the in vitro production of the inflammatory mediator NO by LPS-stimulated cultured murine macrophages.

Methods:

Macrophage isolation and cell culture—Peritoneal macrophages were collected from the peritoneal cavity of 6-8 week old male ICR mice (Harlan, Israel) that had been given an intraperitoneal injection of 1.5 ml of thioglycollate broth (4%) 4 days before harvest. Peritoneal macrophages were washed three times with PBS, yielding 90-95% purity. Peritoneal macrophages and murine macrophage cell line RAW264.7 were cultured RPMI 1640 medium containing 10% FCS, 2 mM L-glutamine; 100 U/ml penicillin; 100 μg/ml streptomycin (Beit-Haemek, Israel) in 96-well plates ($1×10^6$ cells/well) at 37° C. in 5% $CO_2$ atmosphere. Cells were stimulated with LPS (0.1-1 μg/ml) in the presence or absence of NS oil acid and/or one or more of the following carotenoids: astaxanthin, lutein and beta-Carotene. The following stock solutions of each active agent were used to prepare the various dilutions tested:

Cold-pressed NS oil containing 3% thymoquinone and 1.7% free fatty acids (N.S. Oils, Israel).

Lutein 20% (Lycored Ltd., Israel)

Beta-carotene 30% in vegetable oil (Lycored Ltd., Israel)

Astaxanthin oleoresin extracted from microalgae, containing 10% astaxanthin (Algatech, Israel).

Lycopene (present at a concentration of 6.35% in the commercially-available product known as Lyc-O-Mato, obtained from Lycored Ltd., Israel).

The carotenoids were dissolved in DMSO (to a final concentration of 5 mM). The mixture was vortexed and incubated in a water bath at 37° C. (with shaking) for 10 min and then sonicated in a sonicator bath three times for 15 seconds each time. Using this stock solution, the desired concentrations were prepared by the addition of appropriate volumes thereof to warm culture medium.

Appropriate volumes of DMSO (0.1-0.2%) were added to the control tubes and the percent inhibition of NO production in each test tube was calculated in relation to its control.

NO production assay—NO levels in supernatants of cell cultures were determined by assaying nitrite levels using Griess reagent and sodium nitrite as a standard as described in Green, L. C., Wagner, D. A., Glogowski, J., Skipper, P. L., Wishnok, J. S., and Tannenbaum, S. R. (1982) *Anal Biochem.* 126: 131-138.

Results:

(1) First Study:

The upper left panel of FIG. 1 shows that at the two concentrations tested (0.0015 and 0.0030 μg/ml), NS oil ("Ketzah" in the legends in this and some of the subsequent figures) displayed very low levels of anti-inflammatory activity on this model of NO production, less than 5% of control values in both cases.

The upper right panel of FIG. 1 indicates that astaxanthin (at concentrations of 0.298 and 0.596 μg/ml) more active than NS oil, causing inhibition of NO production of around 20-25% of maximal inhibition.

The middle panel of FIG. 1 presents the results for combinations of 0.298 μg/ml astaxanthin and either 0.0015 or 0.0030 μg/ml NS oil. As may be seen in this figure, both combinations caused a greater than additive (i.e. synergistic) inhibition of NO production. (The predicted, additive values for the two components in combination are indicated by the horizontal line at the top of the shaded portion of each bar in the graph.)

Similarly, as shown in the lower panel of FIG. 1, the higher dose of astaxanthin (0.596 μg/ml) was found to interact synergistically with NS oil at both doses tested.

Figure 2:
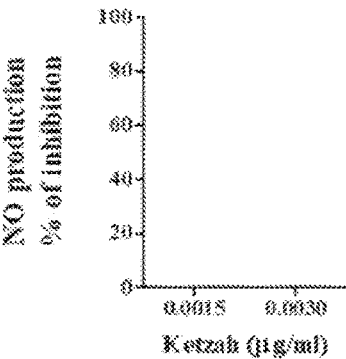
FIG. 2 graphically presents results showing the inhibitory effect of combinations of TG and lutein on NO production.
Figure 2:
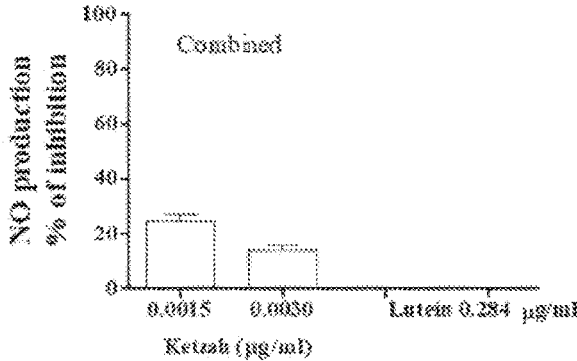
Figure 2:
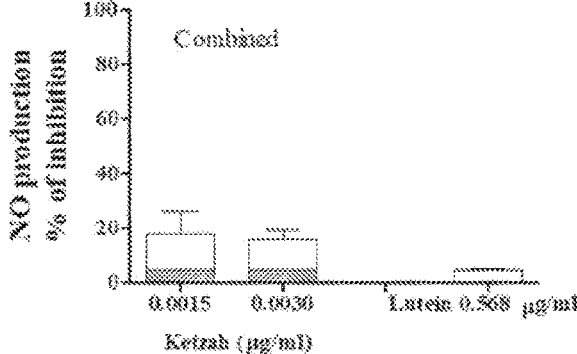

Turning now to the results presented in FIG. 2, the upper graph presents the results for the inhibition of NO product by two different concentrations of NS oil (0.0015 and 0.0030 μg/ml). As shown in the graph, these concentrations did not result in any measurable inhibition of NO production.

The middle graph presents the results for NO inhibition obtained with the carotenoid lutein, Lutein for this experiment, crystalline Lutein concentration 80% when used alone at a concentration of 0.284 μg/ml, and in combination with the two aforementioned concentrations of NS oil. It may be seen from these results that although lutein alone, at this concentration, did not cause any measurable degree of NO inhibition, its combination with NS oil (at both concentrations) did cause significant inhibition. This is clearly a very marked synergistic effect, since neither of the two components of the combination (i.e. lutein and NS oil) caused any inhibition whatsoever when tested alone.

The lower graph presents the results for NO inhibition obtained with the carotenoid lutein, when used alone at a concentration of 0.568 μg/ml, and in combination with the two aforementioned concentrations of NS oil (0.0015 and 0.0030 μg/ml). It may be seen from these results that although lutein alone, at this concentration, caused only a low level of NO inhibition (<1-%), its combination with NS oil (at both concentrations) did cause significant inhibition, much greater than the predicted additive value (indicated by the horizontal line at the upper border of the shaded area of the graph). This result clearly indicates marked synergism between lutein and the NS oil at the concentrations tested.

Figure 3:
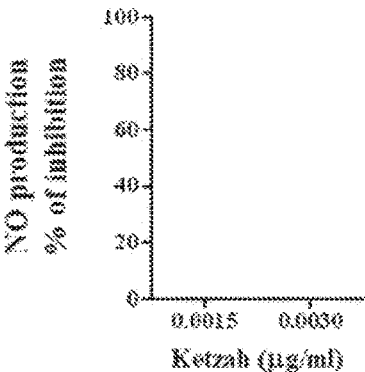
FIG. 3 graphically presents results showing the inhibitory effect of combinations of TG and beta-carotene on NO production.
Figure 3:
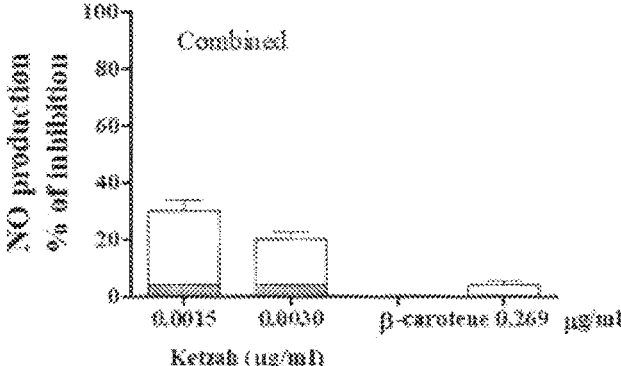
Figure 3:
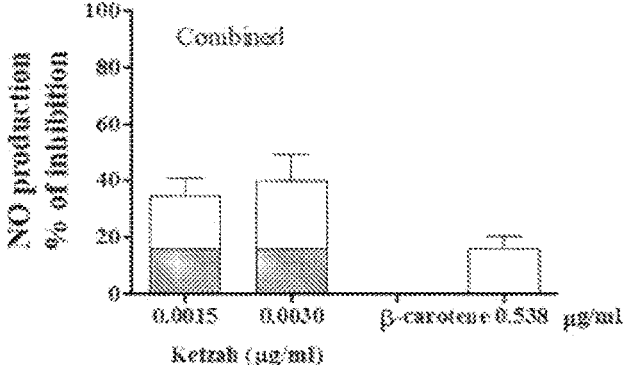

FIG. 3 presents, in the upper graph, results obtained using NS oil alone, at concentrations of 0.0015 and 0.0030 μg/ml. No inhibition of NO production was seen at either concentration.

The middle graph presents the results for NO inhibition obtained with the carotenoid beta-carotene, when used alone at a concentration of 0.269 μg/ml, and in combination with the two aforementioned concentrations of NS oil. It may be seen from these results that beta-carotene alone, at this concentration, caused a low level of NO inhibition (<10%). However, when used in combination with NS oil (at both concentrations) a very marked increase in the amount of NO inhibition was seen, indicating a very high degree of synergistic interaction between the NS oil and beta-carotene.

The lower graph presents the results for NO inhibition obtained with beta-carotene, when used alone at a concentration of 0.538 μg/ml, and in combination with the two aforementioned concentrations of NS oil (0.0015 and 0.0030 μg/ml). It may be seen from these results that although beta-carotene alone, at this concentration, caused a moderate level of NO inhibition of slightly less than 20%. However, when used in combination with NS oil (at both concentrations) a greatly enhanced degree of inhibition was seen (approximately twice that caused by beta-carotene alone). This result clearly indicates marked synergism between beta-carotene and the NS oil at the concentrations tested.

(2) Second Study:

A second set of experiments was performed, using the same methods as described above for the first study. In this second set, combinations of NS oil with a further carotenoid—lycopene—were also tested.

Figure 4:
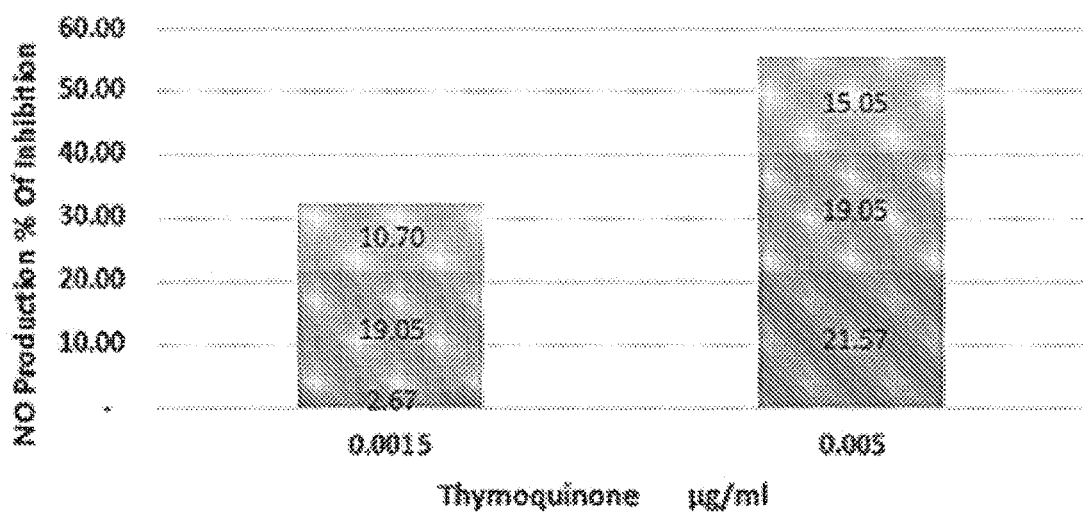
FIG. 4 presents the results of a further study on the inhibitory effect of combinations of TG and astaxanthin on NO production.
Figure 4:
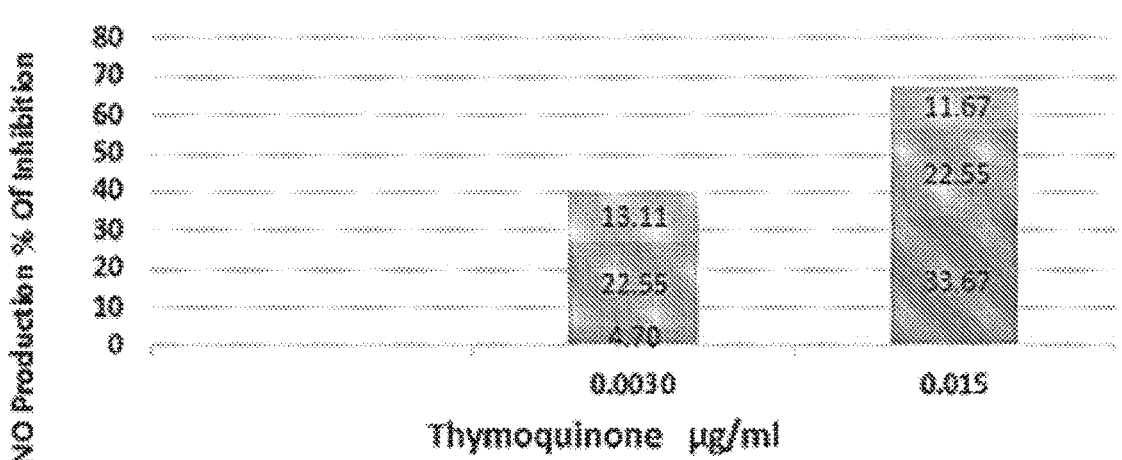

FIG. 4 presents the results for combinations of NS oil and astaxanthin. Thus, in the top graph of this figure, results are shown for combinations of astaxanthin used at a final concentration of 0.298 μg/ml with NS oil containing TQ at a final concentration of either 0.0015 μg/ml (left bar) or 0.005 μg/ml (right bar). In the bottom graph of the figure, results are shown for combinations of astaxanthin used at a final concentration of 0.596 μg/ml with NS oil containing TQ at a final concentration of either 0.0030 μg/ml (left bar) or 0.015 μg/ml (right bar). Each of the bars in this graph (and in the similar bar graphs that follow) contains three stacked segments: a lower segment indicating the degree of percentage inhibition of NO production following treatment with the NS oil alone; a middle segment indicating the percentage inhibition due to astaxanthin alone; a top segment indicating the percentage inhibition caused by a combination of NS oil and astaxanthin at the concentrations indicated. It is to be appreciated that if there were to be only an additive (and not synergistic) interaction between the two active agents, then the top of the bar in FIG. 4 would be level with the top of the middle segment. That is, no third (top) segment would be seen. In the case of a synergistic interaction between the two components, however, the percentage NO inhibition due to the combination of the two active components would be greater than the sum of each separately, and thus the third (top) segment, having a height equivalent to the greater-than-additive effect would be seen. It should be noted that in each of the results plotted in the upper and lower graphs of this figure, a top segment is present, indicating a greater than additive, or synergistic, interaction between the NS oil and astaxanthin.

The upper graph in FIG. 4 shows that at the two TQ concentrations tested (0.0015 and 0.0050 μg/ml), NS oil alone (lower segment of each bar) caused relatively low levels of anti-inflammatory activity in this model of NO production; 2.67% and 21.57%, respectively. Similarly, 0.298 μg/ml astaxanthin, when used alone, caused modest inhibition of NO production (19.05%). However, when 0.298 μg/ml astaxanthin and NS oil (at both concentrations) were used in combination, a clear synergistic effect was observed, with greater than additive results being obtained (upper segment of each bar). A similar synergistic effect was also seen when the combination contained astaxanthin at a higher concentration (0.596 μg/ml; lower graph of FIG. 4).

Figure 5:
FIG. 5 presents the results of a further study on the inhibitory effect of combinations of TG and lutein on NO production.
Figure 5:
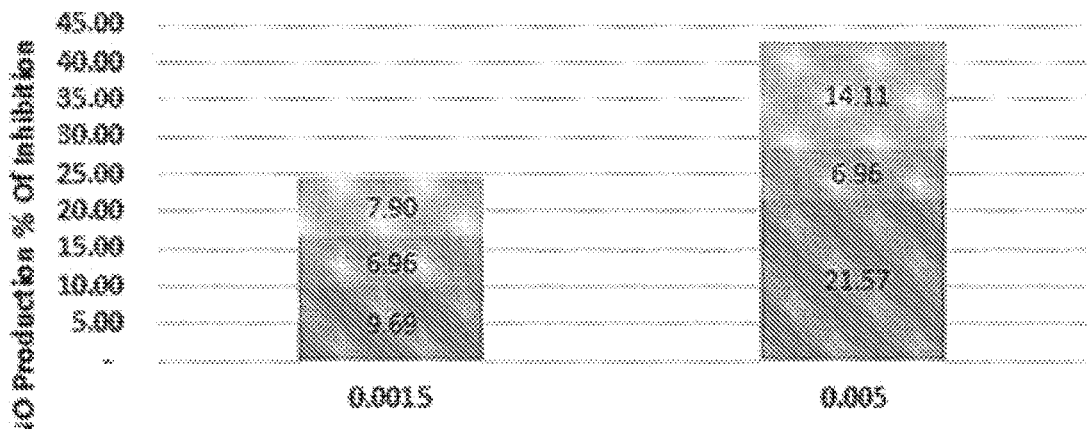
Figure 5:

FIG. 5 presents the results for combinations of NS oil and lutein. Thus, in the top graph of this figure, results are shown for combinations of lutein used at a final concentration of 0.284 μg/ml with NS oil containing TQ at a final concentration of either 0.0015 μg/ml (left bar) or 0.005 μg/ml (right bar). In the bottom graph of the figure, results are shown for combinations of lutein used at a final concentration of 0.568 μg/ml with NS oil containing TQ at a final concentration of either 0.0030 μg/ml (left bar) or 0.015 μg/ml (right bar). It may be seen that in each of the results plotted in the upper and lower graphs of this figure, a top (third) bar segment is present, indicating (as explained hereinabove) a greater than additive, or synergistic, interaction between the NS oil and lutein.

The upper graph in FIG. 5 shows that at the two TQ concentrations tested (0.0015 and 0.0050 μg/ml), NS oil alone (lower segment of each bar) caused relatively low levels of anti-inflammatory activity in this model of NO production; 9.69% and 21.57%, respectively. Similarly, 0.284 μg/ml lutein, when used alone, caused low-level inhibition of NO production (6.96%). However, when 0.284 μg/ml lutein and NS oil (at both concentrations) were used in combination, a clear synergistic effect was observed, with greater than additive results being obtained (upper segment of each bar). A similar synergistic effect was also seen when the combination contained lutein at a higher concentration (0.568 μg/ml; lower graph of FIG. 5) together with NS oil having TQ concentrations of 0.0030 and 0.0150 μg/ml.

Figure 6:
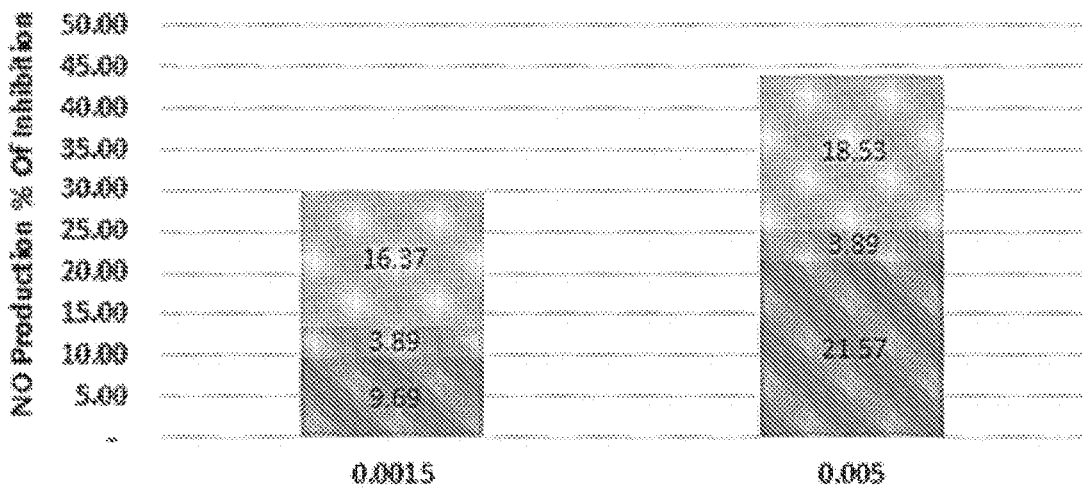
FIG. 6 presents the results of a further study on the inhibitory effect of combinations of TG and beta-carotene on NO production.
Figure 6:
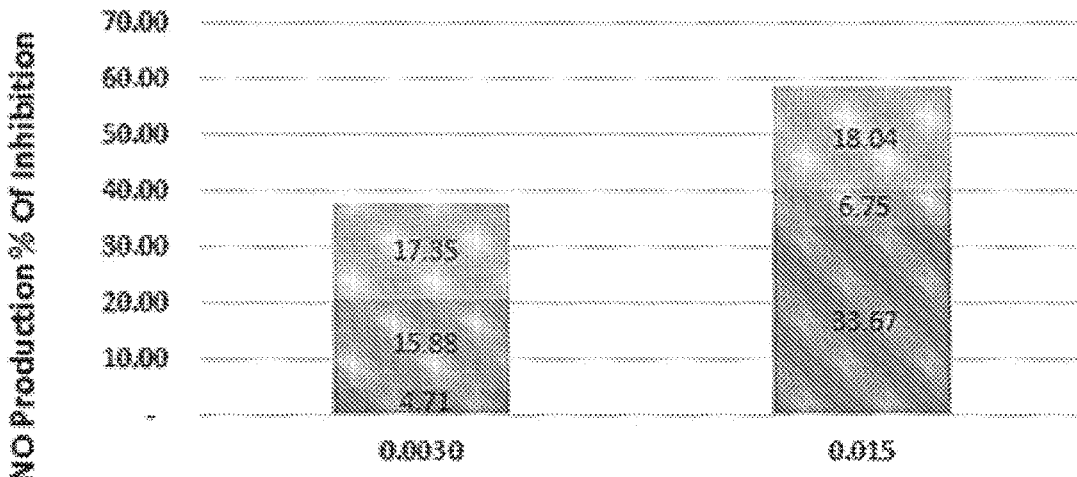

FIG. 6 presents the results for combinations of NS oil and beta-carotene. Thus, in the top graph of this figure, results are shown for combinations of beta-carotene used at a final concentration of 0.269 μg/ml with NS oil containing TQ at a final concentration of either 0.0015 μg/ml (left bar) or 0.005 μg/ml (right bar). In the bottom graph of the figure, results are shown for combinations of beta-carotene used at a final concentration of 0.538 μg/ml with NS oil containing TQ at a final concentration of either 0.0030 μg/ml (left bar) or 0.015 μg/ml (right bar). It may be seen that in each of the results plotted in the upper and lower graphs of this figure, a top (third) bar segment is present, indicating (as explained hereinabove) a greater than additive, or synergistic, interaction between the NS oil and beta-carotene.

The upper graph in FIG. 6 shows that at the two TQ concentrations tested (0.0015 and 0.0050 μg/ml), NS oil alone (lower segment of each bar) caused relatively low levels of anti-inflammatory activity in this model of NO production; 9.69% and 21.57%, respectively. Similarly, 0.269 µg/ml beta-carotene, when used alone, caused low-level inhibition of NO production (3.89%). However, when 0.269 µg/ml beta-carotene and NS oil (at both concentrations) were used in combination, a clear synergistic effect was observed, with greater than additive results being obtained (upper segment of each bar). A similar synergistic effect was also seen when the combination contained beta-carotene at a higher concentration (0.538 µg/ml; lower graph of FIG. 6) together with NS oil having TQ concentrations of 0.0030 and 0.0150 µg/ml.

Figure 7:
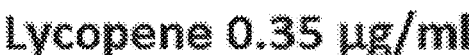
FIG. 7 graphically presents results showing the inhibitory effect of combinations of TG and lycopene on NO production.
Figure 7:
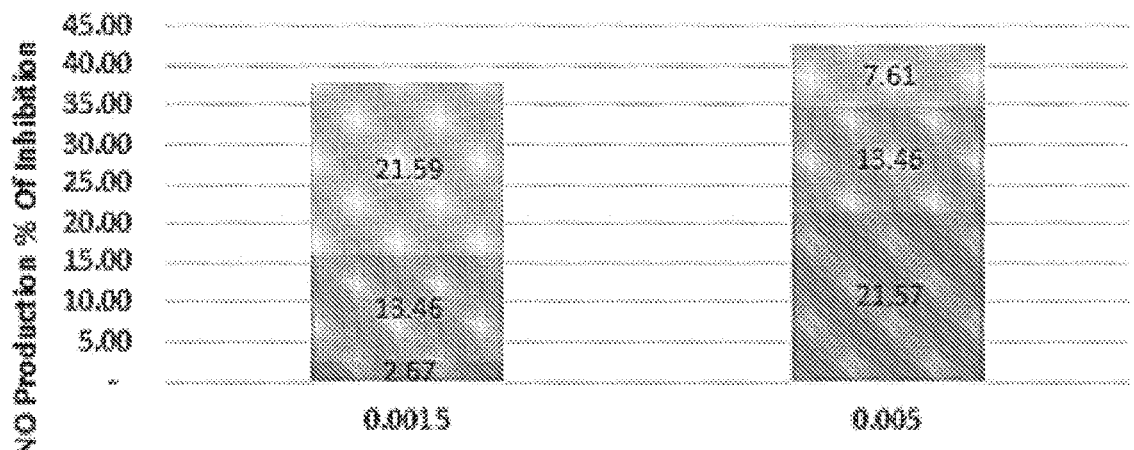
Figure 7:
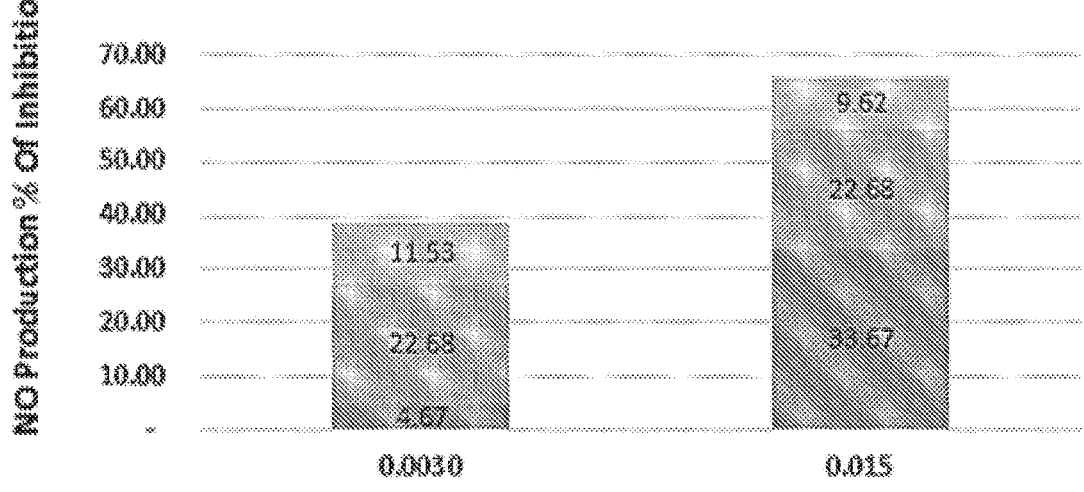

FIG. 7 presents the results for combinations of NS oil and lycopene. Thus, in the top graph of this figure, results are shown for combinations of lycopene used at a final concentration of 0.35 µg/ml with NS oil containing TQ at a final concentration of either 0.0015 µg/ml (left bar) or 0.005 µg/ml (right bar). In the bottom graph of the figure, results are shown for combinations of lycopene used at a final concentration of 0.75 µg/ml with NS oil containing TQ at a final concentration of either 0.0030 µg/ml (left bar) or 0.015 µg/ml (right bar). It may be seen that in each of the results plotted in the upper and lower graphs of this figure, a top (third) bar segment is present, indicating (as explained hereinabove) a greater than additive, or synergistic, interaction between the NS oil and lycopene.

The upper graph in FIG. 7 shows that at the two TQ concentrations tested (0.0015 and 0.0050 µg/ml), NS oil alone (lower segment of each bar) caused relatively low levels of anti-inflammatory activity in this model of NO production; 2.67% and 21.57%, respectively. Similarly, 0.35 µg/ml lycopene, when used alone, caused low-level inhibition of NO production (13.46%). However, when 0.35 µg/ml lycopene and NS oil (at both concentrations) were used in combination, a clear synergistic effect was observed, with greater than additive results being obtained (upper segment of each bar). A similar synergistic effect was also seen when the combination contained lycopene at a higher concentration (0.75 µg/ml; lower graph of FIG. 7) together with NS oil having TQ concentrations of 0.0030 and 0.0150 µg/ml.

Example 2

Inhibition of the Production of Nitric Oxide (NO) by Various Combinations of NS Oil and CBD The aim of this study was to investigate the effect of different combinations of NS oil and CBD on the in vitro production of the inflammatory mediator NO by LPS-stimulated cultured murine macrophages.

Methods:

The methods used were the same as those described in Example 1. CBD was provided in the form of hemp oil containing 15% CBD, obtained from RAD Extracts USA.

Figure 8:
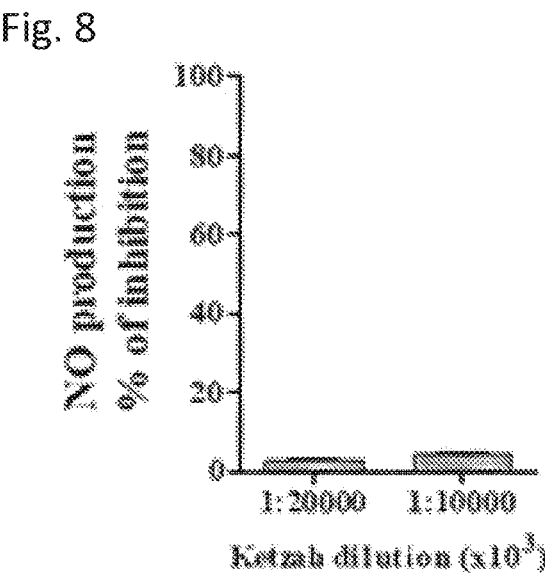
FIG. 8 graphically presents results showing the inhibitory effect of combinations of TG and CBD on NO production.
Figure 8:
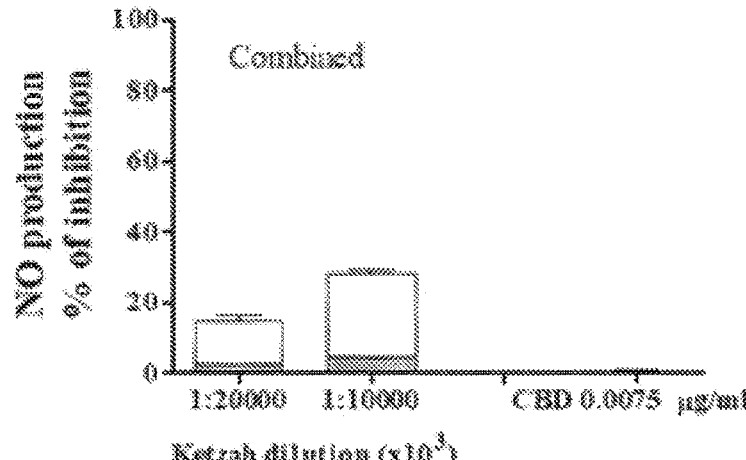
Figure 8:
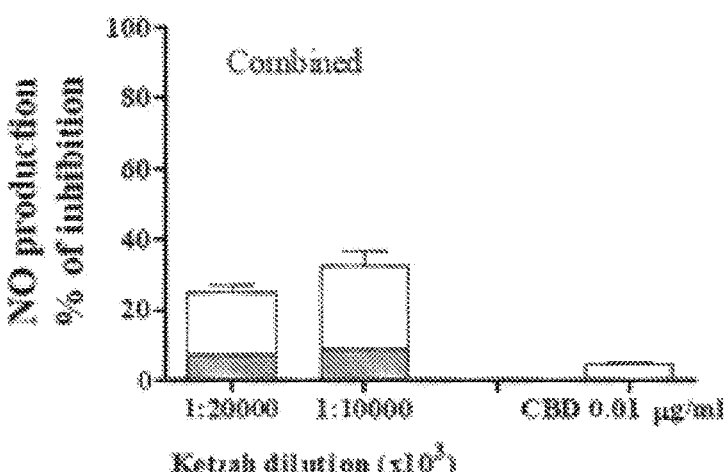

Results:

(1) First Study:

The upper graph of FIG. 8 presents results obtained using NS oil alone, at dilutions of 1:20,000 and 1:10,000. Low-level inhibition of NO production (<10%) was seen at both of these dilutions.

The middle graph presents the results for NO inhibition obtained with CBD, when used alone at a concentration of 0.0075 µg/ml, and in combination with the two aforementioned dilutions of NS oil. It may be seen from these results that treatment with CBD alone, at this concentration, did not results in a detectable level of NO inhibition. However, when used in combination with NS oil (at both dilutions) a very marked increase in the amount of NO inhibition was seen, indicating a very high degree of synergistic interaction between the NS oil and CBD.

The lower graph presents the results for NO inhibition obtained with CBD when used alone at a concentration of 0.01 µg/ml, and in combination with the two aforementioned dilutions of NS oil (1:20,000 and 1:10,000). It may be seen from these results that although CBD alone, at this concentration, caused a low level of NO inhibition of less than 10%.

However, when used in combination with NS oil (at both dilutions) an enhanced degree of inhibition was seen. This result clearly indicates marked synergism between CBD and NS oil at the concentrations tested.

(2) Second Study:

A further study, aimed at confirming the findings of the initial study, reported above, was performed using the same methods and materials described hereinabove. Combinations of CBD (at three different concentrations) and NS (at four different TQ concentrations) were tested, and the results shown in FIG. 9, in the form of segmented bar graphs. As explained hereinabove, in Example 1, the lower segment of each bar graph represents the percentage inhibition of NO production caused by NS oil alone, the middle segment shows the percentage inhibition caused by CBD alone and the upper segment shows the greater-than-additive (i.e. synergistic) inhibition caused by a combination of both NS oil and CBD.

Figure 9:
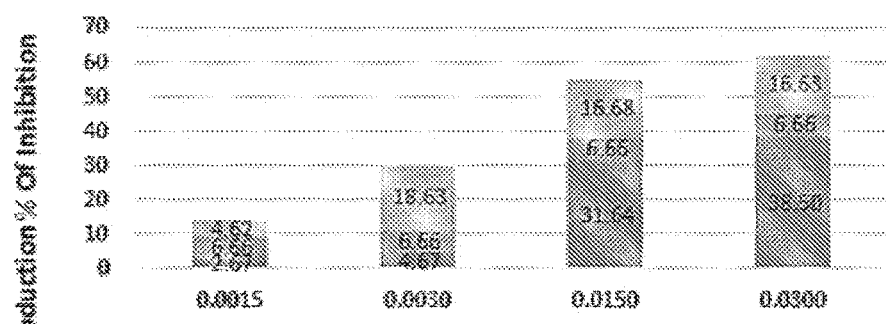
FIG. 9 presents the results of a further study on the inhibitory effect of combinations of TG and CBD on NO production.
Figure 9:
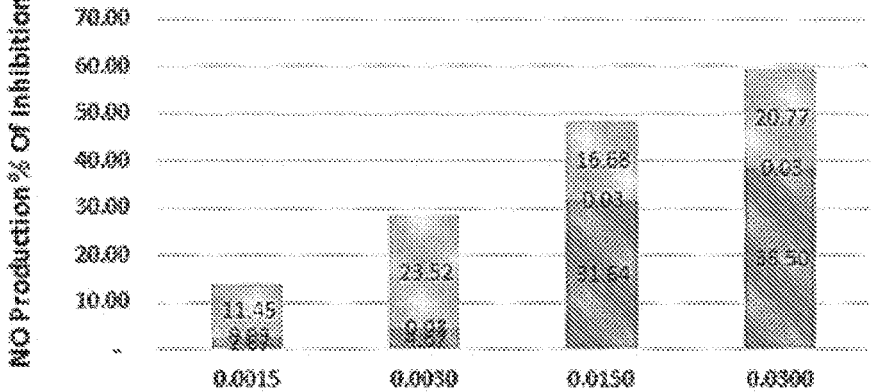
Figure 9:
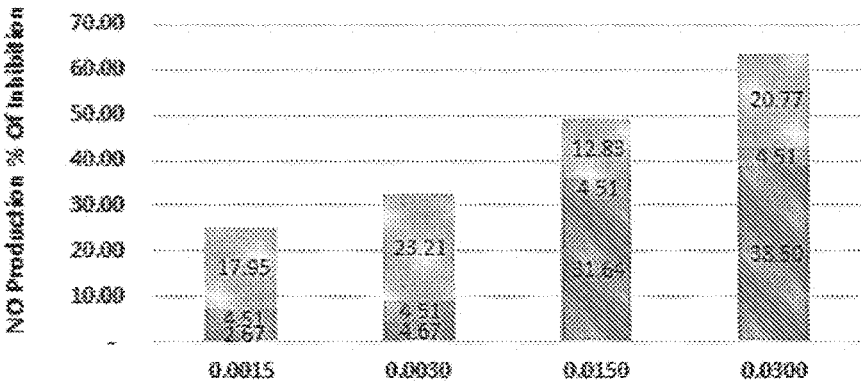

The upper graph of FIG. 9 presents data for compositions comprising 0.005 µg/ml CBD. As may be seen from this graph, both NS oil alone (lower segments) and CBD alone (middle segments) caused measurable inhibition of NO production. However, at each TQ concentration tested, the composition comprising a combination of TQ and CBD caused a greater-than-additive (i.e. synergistic) inhibition (upper segment of each graph). Similar results were also seen when CBD was used at higher concentrations (0.0075 µg/ml and 0.01 µg/ml; middle and lower graphs, respectively).

Example 3

Inhibition of the Production of Nitric Oxide (NO) by Various Combinations of NS Oil and Pycnogenol Pycnogenol is a food supplement derived from extracts of maritime pine bark and is standardized to contain 70% procyanidin. The use of pycnogenol for the prevention and/or treatment of several different conditions has been proposed. The aim of the present study was to investigate the effect of different combinations of NS oil and pycnogenol on the in vitro production of the inflammatory mediator NO by LPS-stimulated cultured murine macrophages.

Methods:

The methods used were the same as those described in Example 1. The Pycnogenol used was a maritime pine extract obtained from Biolandes (catalogue number F0400).

Results:

The effects of 100 µg/ml pycnogenol and three different dilutions of NS oil (having TQ concentrations of 0.0015, 0.003 and 0.015 µg/ml) on NO production, when used both separately and in combination were tested. The results are shown in FIG. 10, in the form of three segmented (or stacked) bar graphs, corresponding, from left to right, to TQ concentrations of 0.0015, 0.003 and 0.015 µg/ml, respectively.

Figure 10:
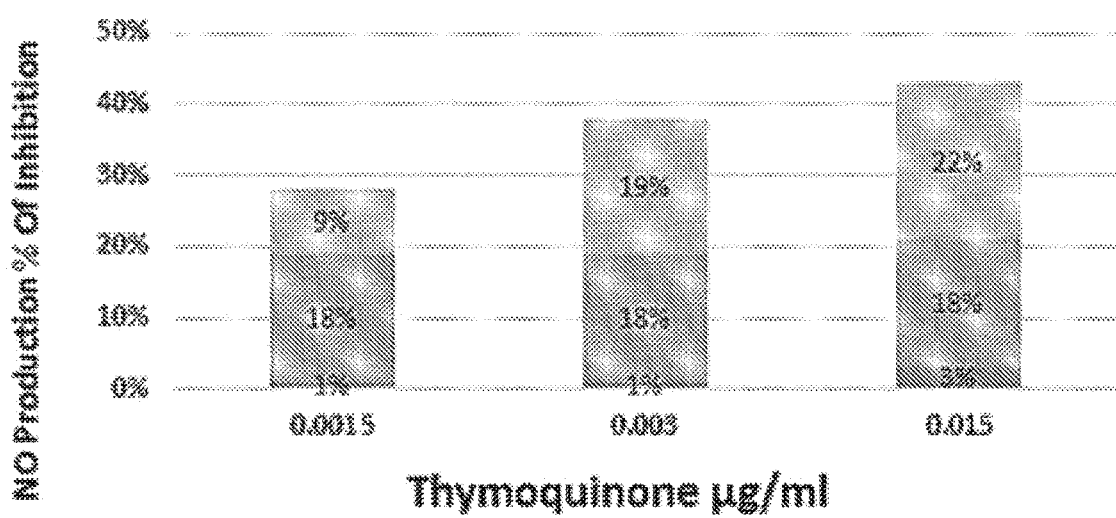
FIG. 10 graphically presents results showing the inhibitory effect of combinations of TG and Pycnogenol on NO production.

It is clear from the results presented in FIG. 10 that NS oil alone (bottom segment of each graph) at each of the three TQ concentrations tested caused low-level inhibition of NO production (1-3%). Pycnogenol, at the concentration tested caused moderate inhibition of NO production (middle segment of each graph; 18%). However, the combination of 100 μg/ml pycnogenol with NS at each of the three dilutions caused inhibition of NO production that was greater than the expected additive value, as witnessed by the additional 9%, 19% and 22% inhibition seen with the combinations comprising 0.0015, 0.003 and 0.015 μg/ml TQ, respectively (upper segment of each bar).

Example 4

Comparative Example: Non-Synergistic Interaction Between High-FFA NS Oil and Astaxanthin with Regard to the Inhibition of the Production of Nitric Oxide (NO)

The synergistic interactions between NS oil and other biologically active agents that were reported in the previous examples, hereinabove, were seen when the NS oil chosen was a cold-pressed oil having a high TQ concentration (3%) and a low free fatty acid (FFA) (1.7%). Without wishing to bound by theory, the present inventors believe that said synergistic interaction is obtained only when the NS oil used is characterized by aforesaid high TQ and low FFA concentrations. The present comparative study was performed in order to test this hypothesis by measuring the anti-inflammatory activity of a combination of astaxanthin and a cold-pressed NS oil having a relatively low TQ concentration (1.15%) and a relatively high FFA concentration (5%). Methods:

The methods and materials used were the same as those described in Example 1, with the exception of the cold-pressed NS oil used in this study. This oil was obtained from Amazing Herbs and had the following composition:

| p-Cymene avg % | TQ avg % | Carvacrol avg % | FFA by titration, % as oleic acid |
|---|---|---|---|
| 0.72 | 1.15 | 0.05 | 5.00 |

Results:

The NO production percentage inhibition results obtained for two dilutions of the NS oil (one having a TQ concentration of 0.0015 μg/ml and the other having a TQ concentration of 0.0030 μg/ml) and one concentration of astaxanthin (0.298 μg/ml) are summarized in the following table:
Inhibition of NO Production:

| Test agent: | TQ concentration of NS oil dilution | |
| | 0.0015 μg/ml TQ | 0.0030 μg/ml TQ |
|---|---|---|
| High-FFA NS oil only | 0% | 0% |
| Astaxanthin only | 19.05% | 21.26% |
| Combination of high-FFA NS oil and astaxanthin | 13.45% | 11.45% |
| Predicted additive result | 19.05% | 21.26% |
| Difference between obtained and predicted results for the combination | −5.60% | −9.81% |

It may be seen from this table that neither high-FFA NS oil dilution, when tested alone, caused any inhibition of NO production. It is be noted that the TQ concentrations of these dilutions were the same as those of the low-FFA oil tested in Example 1, and which were found to inhibit NO production (see FIG. 1). Astaxanthin only, however, did cause significant inhibition of NO production (approximately 20% inhibition). Since the NS oil alone was inactive in this study, the predicted additive value for inhibition caused by the combination of that oil with astaxanthin would be the same as the value obtained with astaxanthin alone (see table, above). However, the actual results obtained for this combination were in fact lower than this predicted additive result (5.60% and 9.81% lower, respectively, for the 0.0015 and 0.003 μg/ml TQ concentrations).

Figure 11:
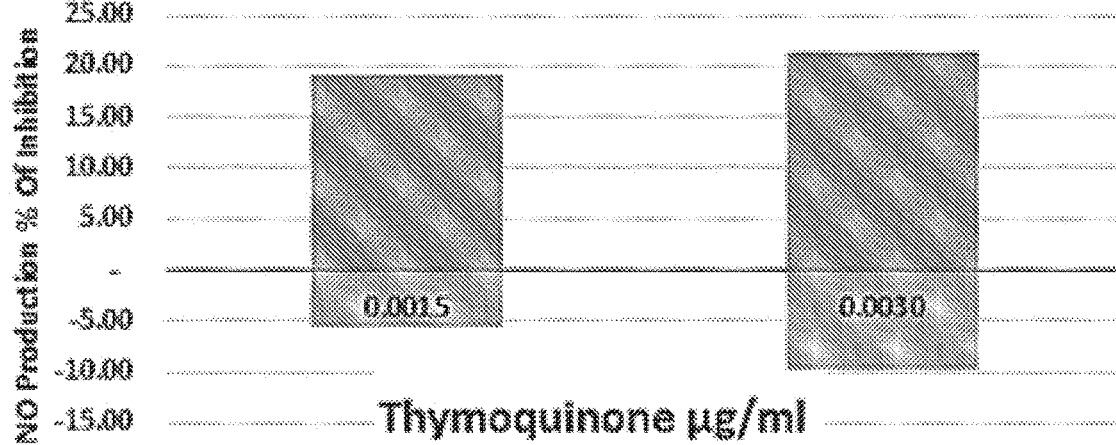
FIG. 11 graphically presents the results of a comparative example, in which the effect of a combination of NS oil having a high concentration of FFA together with astaxanthin is studied.

These results are also summarized graphically in FIG. 11.

We may conclude from these results that when the NS oil used to prepare the dilutions is one having a relatively low TQ concentration (i.e. 1.15%) and a relatively high FFA concentration (i.e. 5%), then there is no positive synergistic anti-inflammatory interaction between said NS oil and other active agents such as astaxanthin.

The following formulation examples illustrate some specific dosage forms containing compositions of the present invention. These examples are for illustrative purposes only and are not intended to limit the scope of the claimed invention any way.

Formulation Example 1

Softgel Capsules Containing Combinations of Astaxanthin and NS Oil
1.1 Primary Active Ingredients:

| Astaxanthin | 5 mg |
| NS oil (3% TQ) | 500 mg |

Other Ingredients:
    Modified tapioca starch
    Safflower oil
    Glycerin
    Purified water
    Annatto
1.2 Primary Active Ingredients:

| Astaxanthin | 5 mg |
| NS oil (3% TQ) | 33 mg |

Other Ingredients:
    Modified tapioca starch
    Safflower oil
    Glycerin
    Purified water
    Annatto Formulation Example 2

Softgel Capsules Containing Combinations of Lutein and NS Oil
2.1 Primary Active Ingredients:

| Lutein | 20 mg |
| NS oil (3% TQ) | 33 mg |

Other Ingredients:
  Modified tapioca starch
  Safflower oil
  Glycerin
  Purified water
  Annatto
2.2 Primary Active Ingredients:

| | |
|---|---|
| Lutein | 20 mg |
| NS oil (3% TQ) | 500 mg |

Other Ingredients:
  Modified tapioca starch
  Safflower oil
  Glycerin
  Purified water
  Annatto

The invention claimed is:

1. A composition comprising a combination of thymoquinone (TQ) and astaxanthin, wherein the weight ratio of said TQ to said astaxanthin is in the range of 1:1 to 1:200, wherein the composition is characterized by synergism between said TQ and said astaxanthin with respect to their inhibition of nitric oxide production, and wherein said TQ is present in a cold-pressed oil obtained from *Nigella sativa* seeds.

2. The composition according to claim 1, further including one or more cannabinoids.

3. The composition according to claim 2, wherein the cannabinoid is cannabidiol (CBD).

4. The composition according to claim 3, wherein the CBD is contained in a hemp extract.

5. The composition according to claim 1, further including pycnogenol.

6. The composition according to claim 1, wherein the concentration of TQ is at least 1.5% (w/w), and wherein the composition further comprises free fatty acids (FFA) at a concentration of not more than 3.5% (w/w).

7. The composition according to claim 1, wherein the concentration of TQ is at least 1.5% (w/w).

8. The composition according to claim 7, wherein the concentration of TQ is at least 2% (w/w).

9. The composition according to claim 1, wherein said composition further comprises free fatty acids (FFA) at a concentration of not more than 3.5% (w/w).

10. The composition according to claim 9, wherein the weight ratio of FFA to TQ is equal to or less than 2.33:1.

11. The composition according to claim 10, wherein the weight ratio of FFA to TQ is equal to or less than 1:1.

12. The composition according to claim 1, wherein the concentration of said TQ in said composition is at least 1.5% (w/w), and wherein said composition further comprises FFA at a concentration of no more than 3.5% (w/w).

13. A method for inhibiting nitric oxide production in a subject, comprising administering to the subject an effective amount of a composition according to claim 1.

* * * * *